(12) United States Patent
Daphna et al.

(10) Patent No.: US 11,737,919 B2
(45) Date of Patent: Aug. 29, 2023

(54) ENDOTHELIAL OCULAR IMPLANT

(71) Applicant: EyeYon Medical Ltd., Nes Ziona (IL)

(72) Inventors: Ofer Daphna, Beit Elazari (IL);
Dmitry Dubson, Rehovot (IL); Nahum Ferera, Petah Tikva (IL)

(73) Assignee: EyeYon Medical Ltd., Nes Ziona (IL)

( * ) Notice: Subject to any disclaimer, the term of this patent is extended or adjusted under 35 U.S.C. 154(b) by 135 days.

(21) Appl. No.: 17/349,946

(22) Filed: Jun. 17, 2021

(65) Prior Publication Data
US 2022/0401262 A1    Dec. 22, 2022

(51) Int. Cl.
*A61F 9/007* (2006.01)
*A61F 2/14* (2006.01)
*C08L 33/12* (2006.01)

(52) U.S. Cl.
CPC .......... *A61F 9/00781* (2013.01); *A61F 2/142* (2013.01); *C08L 33/12* (2013.01); *A61F 2250/0091* (2013.01)

(58) Field of Classification Search
CPC ................ A61F 2/142; A61F 9/00781; A61F 2250/0091
See application file for complete search history.

(56) References Cited

U.S. PATENT DOCUMENTS

| | | | |
|---|---|---|---|
| 7,776,086 B2 * | 8/2010 | Miller | A61F 2/142 623/6.23 |
| 9,486,311 B2 * | 11/2016 | Argento | B32B 27/08 |
| 2010/0069915 A1 * | 3/2010 | Shiuey | A61F 2/147 606/107 |
| 2010/0185281 A1 * | 7/2010 | Daphna | A61F 2/14 623/5.11 |
| 2015/0005876 A1 * | 1/2015 | Goldberg | A61F 2/142 623/5.15 |
| 2018/0177587 A1 * | 6/2018 | Anderson | A61P 27/10 |
| 2018/0361018 A1 * | 12/2018 | Shiuey | C08L 25/06 |
| 2019/0159890 A1 * | 5/2019 | Salahieh | A61F 2/1635 |
| 2019/0209377 A1 | 7/2019 | Daphna | |
| 2020/0170786 A1 * | 6/2020 | Daphna | A61F 2/142 |
| 2021/0113375 A1 | 4/2021 | Peyman | |

FOREIGN PATENT DOCUMENTS

| | | |
|---|---|---|
| WO | 2009/146151 | 12/2009 |
| WO | 2020/115605 | 6/2020 |

OTHER PUBLICATIONS

PCT Search Report PCT/IB2022/055461, dated Oct. 11, 2022.

* cited by examiner

*Primary Examiner* — Susan S Su
*Assistant Examiner* — Ted Yang
(74) *Attorney, Agent, or Firm* — Dekel Patent Ltd.; David Klein

(57) ABSTRACT

An ocular implant is constructed of a clear, transparent, biologically compatible material and includes a hydrophilic outer surface configured for continuous attachment to a posterior surface of a cornea. The ocular implant has a first radius of curvature at initial attachment to the posterior surface of the cornea and a second radius of curvature at post-initial attachment to the posterior surface of the cornea. The first radius of curvature is different than the second radius of curvature. The ocular implant remains attached to the posterior surface of the cornea at both the first and second radii of curvature.

22 Claims, 3 Drawing Sheets

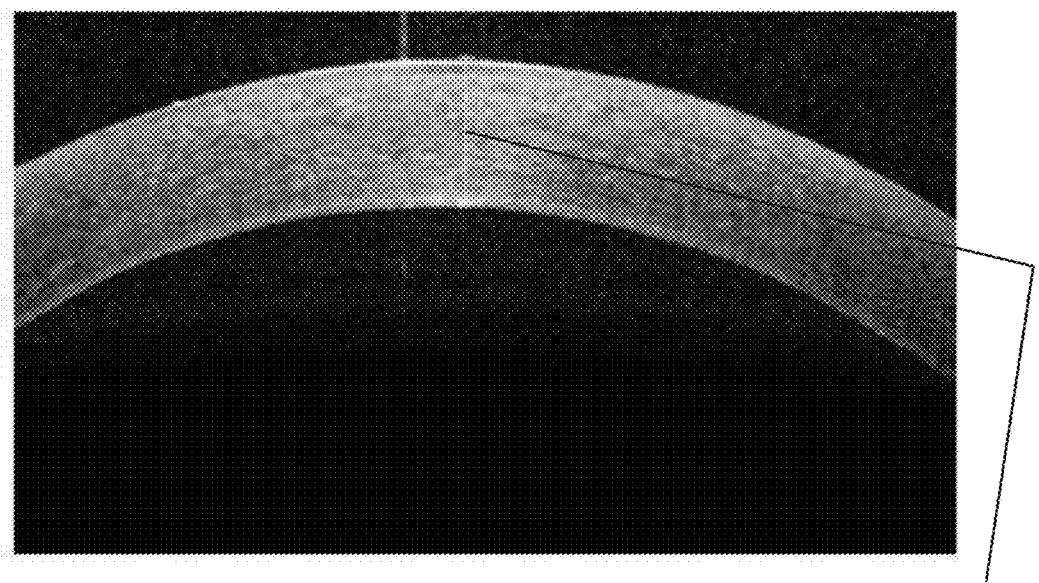
FIG. 5A    THICKNESS = 1159 MICRONS
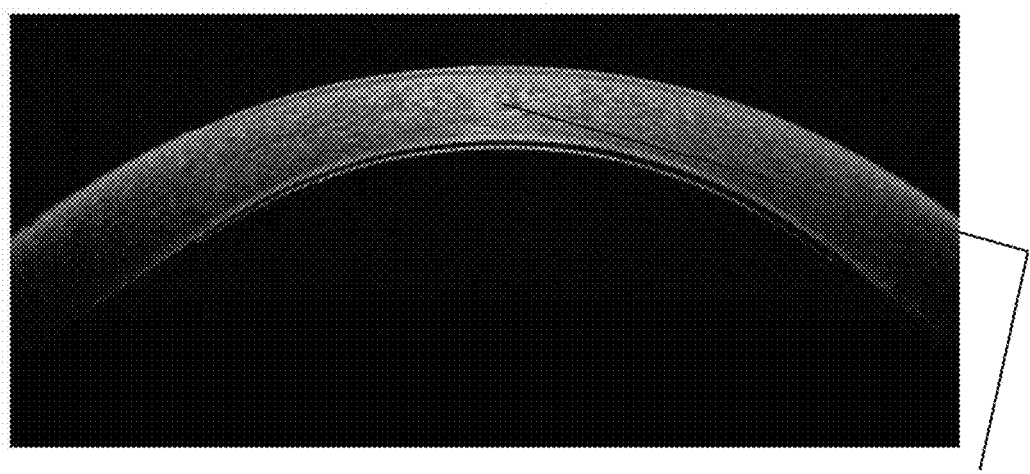
FIG. 5B    THICKNESS = 556 MICRONS
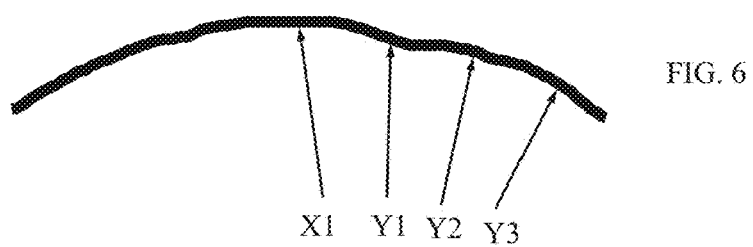
FIG. 6

ENDOTHELIAL OCULAR IMPLANT

FIELD OF THE INVENTION

The present invention relates generally to endothelial ocular implants for treating an over-hydrated, edematous cornea.

BACKGROUND OF THE INVENTION

The quality of the eye's sensory function greatly depends on the qualities of light conduction through the cornea and through the lens, the optical qualities of these organs and the transparency of the cornea and the eye lens, and other factors.

Corneal transparency generally depends on the ability of the cornea to remain in a dehydrated state, and is normally maintained at about a 78% hydration level. The cornea dehydrated state is affected by several interdependent factors, the most important of which is an active pump present in the deepest cell layer of the cornea, the endothelium. Any disruption of the endothelial function beyond a certain level as a result of surgery, trauma, infection, or congenital predisposition results in influx of water to all layers of the cornea thus distorting its transparency. The morbidity of this situation is not only a significant decrease in vision, but also at an advanced state may result in significant pain and scars, a situation known as bullous keratopathy.

Another factor affecting corneal hydration is the stromal swelling pressure (SP), which is the tendency of stroma to swell due to interfibrillary proteoglycans and other proteins. The normal stromal pressure is a positive pressure of 55 mm Hg. Imbibition pressure (IP) is a negative pressure exerted by glycosaminoglycans by which fluid is drawn into the cornea. Intraocular pressure (IOP) is the sum of the stromal swelling pressure and the imbibition pressure. When the IOP (>50-60 mm Hg) exceeds the stromal pressure, epithelial edema occurs. For example, high IOP and normal SP is indicative of acute glaucoma, whereas normal IOP and low SP is indicative of endothelial dystrophy.

The epithelium offers twice the resistance to water flow compared to the endothelium and the electrolyte resistance is 200 times higher in the epithelium than the endothelium. The endothelium pump function ensures, through active transport, the passage of fluid out of the corneal stroma into the aqueous humor. The corneal endothelial permeability gradually increases as central endothelial cell density decreases below 2000 cells/mm$^2$. Compensatory metabolic pump mechanisms maintain the dehydrated state until a central endothelial density of about 500 cells/mm$^2$ is reached.

Another factor affecting corneal hydration is tear evaporation. Normal tear evaporation (a rate of about 2.5 ml/cm$^2$/hour) makes the tear hypertonic resulting in osmotic extraction thus thinning the cornea by 5%. Dehydration works by water evaporating from the tear film, which leaves behind a more concentrated solution at the surface of the eye, causing the tear film to be more hypertonic. The hypertonic tear film draws more water by osmosis from the cornea itself; the opposite is true during the night, when the eyelids are closed. Evaporation can be a factor in maintaining epithelial dehydration, as is observed in the diurnal variations of visual acuity in patients with early stage Fuchs' endothelial dystrophy.

SUMMARY OF THE INVENTION

The present invention relates to an endothelial ocular implant for treatment of corneal edema, as is described more in detail hereinbelow.

There is provided in accordance with an embodiment of the present invention an ocular implant constructed of a transparent, biologically compatible material and including a hydrophilic outer surface configured for continuous attachment to a posterior surface of a cornea, wherein the ocular implant has a first radius of curvature at initial attachment to the posterior surface of the cornea and a second radius of curvature at post-initial attachment to the posterior surface of the cornea, the first radius of curvature being different than the second radius of curvature, and wherein the ocular implant remains attached to the posterior surface of the cornea at both the first and second radii of curvature.

BRIEF DESCRIPTION OF THE DRAWINGS

The present invention will be understood and appreciated more fully from the following detailed description taken in conjunction with the drawings in which:

FIGS. 5A and 5B are simplified photographs of the implant, respectively, initially attached to the swollen and thickened posterior corneal surface, and attached after treating the edema.

FIG. 6 is a simplified illustration of an embodiment of the implant which has multiple radii of curvature.

DETAILED DESCRIPTION OF EMBODIMENTS

Figures 1A, 1B, 1C:
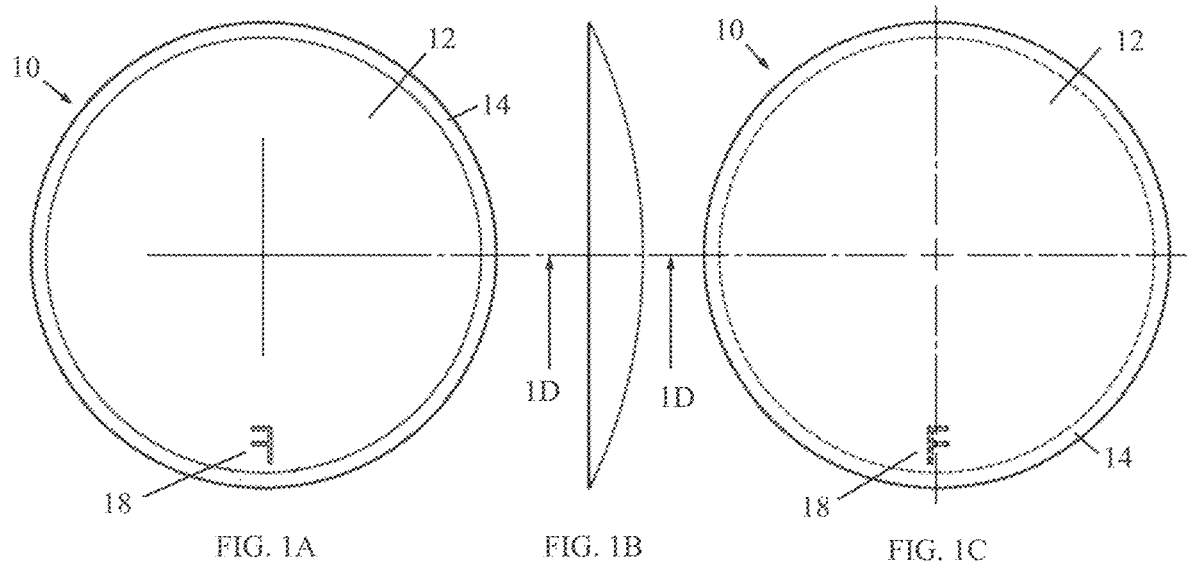
FIGS. 1A, 1B and 1C are simplified rear view, side view and front view illustrations of an endothelial implant, constructed and operative in accordance with an embodiment of the present invention.

Reference is now made to FIGS. 1A, 1B, 1C, 1D and 2, which illustrate a corneal implant 10, constructed and operative in accordance with an embodiment of the present invention. The implant 10 may be a pseudo-endothelial implant, which can be used instead of an implant from a donor in a DSEK (Descemet Stripping Endothelial Keratoplasty) or DMEK (Descemet Membrane Endothelial Keratoplasty) surgery. Implant 10 serves as a water barrier enabling the dehydration of the cornea.

Implant 10 may be constructed of a clear, transparent, biologically compatible material, such as but not limited to, polymethylmethacrylate (PMMA), silicone, silicone rubber, collagen, hyaluronic acid (including the sodium, potassium and other salts thereof), hydrogel, such as acrylic or methacrylic hydrogels, e.g., hydroxyethyl methacrylate or methacrylic acid copolymer/partially hydrolyzed poly(2-hydroxyethyl methacrylate) (known as PolyHEMA), polysulfones, thermolabile materials and other relatively hard or relatively soft and flexible biologically inert optical materials, or any combination of such materials, such as a gel encapsulated in a polymer. Implant 10 may thus be rigid, semi-rigid or foldable, for example.

Some or all of implant 10 may be hydrophilic or hydrophobic.

In a preferred embodiment of the invention, implant 10 is made of a copolymer of hydroxyethyl methacrylate and methyl methacrylate, commercially available as Ci26 from Contamac Ltd., Saffron Walden, Essex, UK. This material has excellent machining characteristics, refractive index and foldability. The mechanical properties ensure the implant can be folded and injected easily while allowing for a smooth and controlled unfolding.

Ci26 is a random, crosslinked, acrylate based copolymer consisting of poly[(methylmethacrylate)-co-(2-hydroxyethyl methacrylate)-co-(ethylene glycol dimethacrylate)], that is, it is a copolymer of methylmethacrylate (MMA) and 2-hydroxyethyl methacrylate (HEMA) and ethylene glycol dimethacrylate (EGDM). Methyl methacrylate (MMA) is a hydrophobic monomer that forms a homopolymer that does not substantially absorb water. 2-hydroxyethyl methacrylate (HEMA) is a modification of MMA, in which the non-polar pendant methyl group of MMA is replaced with a polar hydroxyethyl functional group. When HEMA is made into a homopolymer (pHEMA), it retains a hydrophobic backbone structure but the polar pendant groups allow water to be absorbed into the polymer matrix. Fully hydrated hydrogels of pHEMA typically contain up to 40% water by weight.

EGDM contains two methacrylate functionalities polymerized to form cross-links between the polymer chains, MMA and HEMA, and is hydrophobic in nature.

Ci26 is a blend of approximately 14% MMA, 85% HEMA, and <1% of EGDM, producing a material that can absorb water, and when fully hydrated will contain 26% water by weight. The material therefore contains a mixture of both hydrophilic and hydrophobic components.

According to CONTAMAC, the manufacturer of Ci26, Ci26 is manufactured in accordance with the following steps:

a. The raw materials (MMA, HEMA and EGDM) are mixed together.

b. The mixture is poured into molds (e.g., rod molds) and placed in a polymerization bath.

c. Once polymerized, the material is annealed to remove internal stresses and toughen the material.

d. The annealed material is then machined into blanks and sold in the form of these blanks.

When Ci26 is hydrated and in an aqueous environment, the polar pendant hydroxy groups orientate themselves outward from the surface giving a hydrophilic character on the external surface. In air or non-aqueous environment, those hydrophilic pendant groups orientate themselves inwards, so that the hydrophobic backbone and methyl groups are then presented to the external surface. As a consequence of the above, the chemical nature of Ci26 material contains both hydrophobic and hydrophilic elements, and the external surface is hydrophilic in an aqueous environment and hydrophobic in a non-aqueous environment.

A summary of the specifications for Ci26 is as follows:

Tensile strength=2.5 MPa±10%

Young's modulus=3.0 MPa±10%

Elongation=250%±10%

(per ASTM (American Society for Testing and Materials) D-638 (standard for testing tensile strength, Young's modulus and elongation of plastics)

Water content=26% (after hydration)±10% at 20° C.

Swelling after hydration at 20° C.=1.13 (swelling is calculated as:

$(w2-w1)/(w1)$ wherein $w1$=weight of the polymer (before swelling) and $w2$=weight of the polymer (After swelling)

Refractive index=1.458±10% @35° C. (per ASTM D-542, standard for testing refractive index of plastics)

The implant has the ability to change its radius of curvature to follow the contour of the healing cornea (more about this further below with reference to FIGS. 4A-5B), and yet retains its shape, mechanical, physical and optical properties at all radii of curvature. Additionally, the implant can be folded to enter small incisions in the eye and yet retain its shape, mechanical, physical and optical properties after unfolding in situ in the eye. These features are achieved, without limitation, by annealing the material of which the implant is made (e.g., Ci26), which removes internal stresses and increases the flexibility of the material, while at the same time toughening the material to retain its shape, mechanical, physical and optical properties after unfolding. Other properties that help achieve these features include, without limitation, the viscoelastic nature of the material, its tensile strength, Young's modulus and elongation properties. For example, the above listed tensile strength, Young's modulus and elongation properties of Ci26, and its viscoelastic nature, enable the implant made of Ci26 to change its radius of curvature to follow the contour of the healing cornea, to retain its shape, mechanical, physical and optical properties at all radii of curvature, and the implant made of Ci26 can be folded to enter small incisions in the eye and yet retain its shape, mechanical, physical and optical properties after unfolding in situ in the eye.

Ci26 has high durability to scratches, to which the implant may be subjected to during production, transportation, and surgical manipulations; this means the scratches may be easily removed by standard mechanical procedures (such as but not limited to, polishing or machining) with no degradation to its mechanical, physical and optical properties.

It has been surprisingly discovered by the inventors that the hydrophilic external surface of the implant made of Ci26 helps adhere the implant to the cornea even without the need for sutures or an additional binding agent. However, optionally, an additional binding agent may be used, and optionally, a suture may be used to temporarily hold the implant in place. During the healing process, long-term adherence of the implant to the corneal tissue is enhanced by bio-active attachment via protein adsorption, mainly fibronectin and laminin.

The Ci26 copolymer is clear and transparent without tending to opacification. It is biologically inert and FDA approved for long term ocular implantations. It is stable for ultraviolet radiation (300-400 nm) for a period of 20 years.

In one aspect of the invention, as shown in FIGS. 1A and 1C, corneal implant 10 has a central portion 12 of about 4 mm in diameter ("about" is ±10% throughout the specification and claims) and a peripheral edge 14 extending outwards from the central portion 12, which has a different geometry than the central portion 12, as is explained below. The central portion 12 may be transparent and may or may not have optical properties, such as positive or negative magnification, astigmatism correction, refraction adjustment and others. The peripheral edge 14 is optional; that is, the invention can be carried out with the central portion 12 alone with no additional peripheral edge 14.

For those embodiments with the peripheral edge, the peripheral edge 14 may be made of the same material as central portion 12. Alternatively, peripheral edge 14 may be made of a different material than central portion 12 and bonded or otherwise attached to central portion 12. The peripheral edge 14 may be transparent but can instead be opaque.

Figure 2:
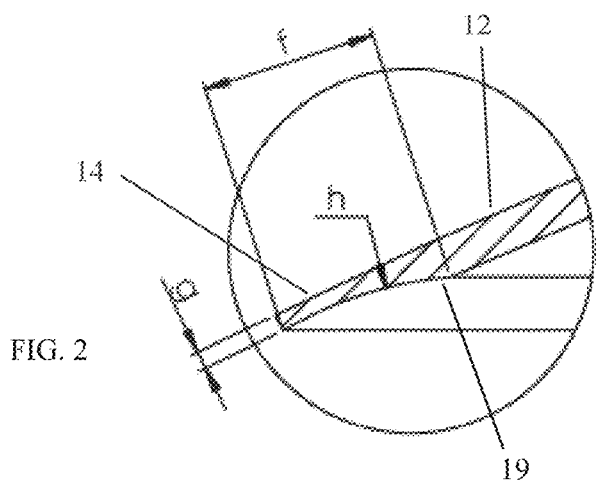
FIG. 2 is an enlarged view of an edge of the implant, indicated by II in FIG. 1D.

As seen in the table below and in FIG. 2, the length of the peripheral edge (also called step length f in the table) may be, without limitation, 0.05-0.2 mm±10%. The radius of the entire implant (half of the implant diameter e in the table) is 1.5-5.0 mm±5%. Thus, for example, for a peripheral edge length of 0.2 mm and implant radius of 3.25 mm, the ratio between the peripheral edge length and the implant radius is 0.0615:1 (that is, the peripheral edge is 6.15% of the total radius. The ratio between the peripheral edge length and the implant radius may be, without limitation, in the range of 0.010-0.133:1.

Figure 1D:
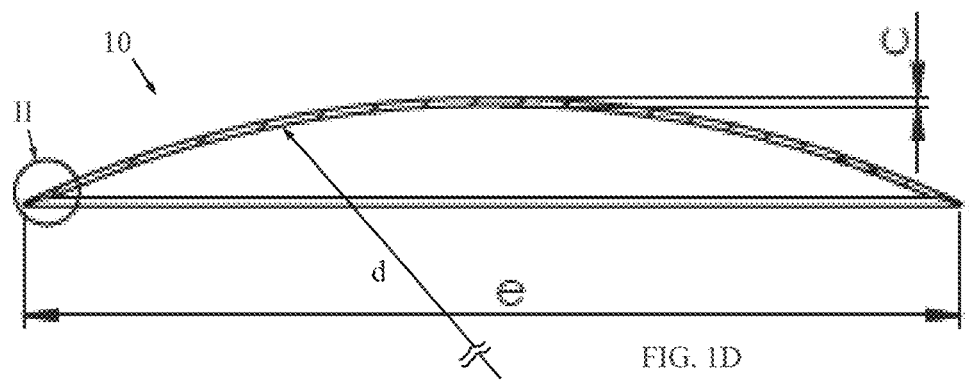
FIG. 1D is a simplified sectional illustration of the implant, taken along lines 1D-1D in FIG. 1B.

Non-limiting dimensions of the implant are as follows, using the nomenclature shown in FIGS. 1D and 2:

| Description | Parameter | Parameter Range [mm] | Tolerance [%] |
| --- | --- | --- | --- |
| Central Thickness | c | 0.03-0.05 | ±15 |
| Base Curve Radius | d | 6.0-8.0 | ±5 |
| Implant Diameter | e | 3.0-10.0 | ±5 |
| Step Length | f | 0.05-0.2 | ±10 |
| Edge Thickness | g | 0.02 | ±15 |
| Edge Curve Radius | h | 0.43 | ±15 |

The base curve radius is the radius of curvature of the implant and will be explained further below with reference to FIGS. 4A, 4B and 4C.

In the illustrated embodiment, the peripheral edge 14 is thinner than the central portion 12 at the juncture of edge 14 with central portion 12, creating a stepped barrier 19. As explained below with reference to FIGS. 3A and 3B, cells (e.g., epithelial cells), proteins or other biomolecules created during the healing process, can proliferate radially inwards on edge 14 up to the stepped barrier 19; this blocks the cells from growing further onto the central portion 12. Thus, the peripheral edge 14 has at least two advantages: a) by being thinner than central portion 12, it is easier for cells, proteins or other biomolecules to proliferate radially inwards on edge 14 as opposed to central portion 12, and b) the stepped barrier 19 blocks the cells from growing further onto the central portion 12.

The implant 10 provides a physical barrier to the passive movement of aqueous humor into the corneal stroma. With the effect of evaporation from the corneal surface, it maintains corneal dehydration and clarity.

Manufacture of Implant 10

Without limitation, implant 10 may be manufactured as follows:

a. Lathe cut process of Ci26 polymer blanks

The implant may be manufactured using lathe cut machinery with a diamond cutting tool controlled by a computer, which generates its final size and curvature. The dimensions and initial curvature of the implant may be custom-made to fit the particular patient.

b. Implant hydration process

The hydration process may be performed by immersing the implant in 0.9% sodium chloride solution for a non-limiting time period of 1-24 hours. At this stage, the implant turns from rigid to flexible and expands to its final hydrated shape.

c. Quality Control (100%): Quality inspection is performed on all implants (100% inspection) for assuring device conformance.

d. Implant packaging and labelling: The implant may be cleaned and packed in ISO class 5 laminar flow cabinet. The implant may be provided within a glass vial filled with 0.9% sodium chloride solution, which serves as a hydration media and a microbiological barrier to ensure the sterility of the product on delivery. In addition, each vial may be packed in a cardboard box, and the vial and box may be tagged with dedicated labels. The packaging materials adequately protect the device from alteration or damage during processing, storage, shipping, handling, and distribution.

e. Device Sterilization: The implant may be sterilized by moist heat sterilization and supplied for a single use. The vial may be sterilized by steam sterilization method.

f. Device final inspection and release.

Insertion of Implant 10

The implant 10 may be inserted into the eye, without limitation, through a 1.8-3.0 mm incision, alternatively a 1.8-2.7 mm incision, alternatively a 1.8-2.4 mm incision, alternatively a 2.0-2.4 mm incision, and preferably a 2.2-2.4 mm incision. The implant may be placed in a suture-less manner or alternatively with one suture for better positioning. The implant may be folded and inserted into the anterior chamber using forceps or a standard IOL injector or a special design injector.

Implantation of the implant 10, without limitation, may be done as follows:

a. Prepare the patient according to standard surgical procedure.

b. Place the patient into position under the surgical microscope.

c. Create a primary entry (e.g., 1.8-2.6 mm) with a keratome side port, and secondary entry point (one or two as necessary) with a stiletto.

d. Optionally, insert anterior chamber maintainer with BSS (balance salt solution) or air e. Optionally, create a descemetorhexis (e.g., 4-8 mm), under BSS or air in the anterior chamber.

f. Open the sterile implant package using and maintaining sterile technique only. Carefully remove the implant using sterile atraumatic instruments.

g. Inspect the implant for damage or defects prior to use.

h. Before insertion, make sure of implant orientation: the peripheral surface of the implant is marked with a mark 18 (FIGS. 1a and 1C), e.g., a number or letter. The mark should appear correctly (that is, as in FIG. 1C, and not a reversed F as in FIG. 1A); otherwise, the implant should be overturned. It is noted that the implant 10 is capable of everting, that is, turning inside out. Nevertheless, the implant material may tend to turn back to its original curved shape, so it is preferable to place the implant in the eye with the proper orientation to avoid the implant from "popping" back to its original orientation. This also applies for the embodiment with the peripheral edge 14.

i. Insert the implant into the eye's anterior chamber with forceps or injector.

j. After insertion ensure the correct placement and orientation of the implant (as explained above); otherwise, the implant should be overturned.

k. Position the implant with an air bubble with respect to the center of pupil.

l. Optionally, inject antibiotic before next step (prior to last air bubble)

m. Suture wound if necessary.

n. Optionally, fill the anterior chamber completely with air, $SF_6$ (sulfur hexafluoride) gas 20% or $C_3F_8$ (octafluoropropane) 10% for 10-90 minutes.

o. After 10-90 minutes reduce air bubble in the anterior chamber to 75%. In case of suspicion of implant instability, consider suturing the implant or using viscoelastic surrounding the implant for better positioning. Alternatively, if there is a good positioning of the implant, approximately 75% air bubbling may be injected initially with no need for further manipulation.

p. Optionally, apply pupil dilatation drops (to prevent pupil block)

q. Leave the patient in a recumbent position facing up for 4 hours after the operation.

r. Instruct the patient to avoid rubbing the eye for the first 48 hours after implantation and use eye shield.

Figure 3A:
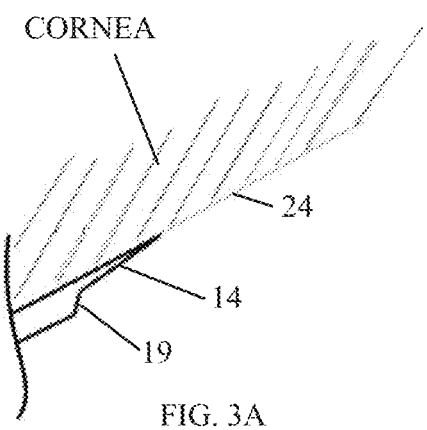
FIGS. 3A and 3B are simplified illustrations of the implant implanted on the posterior corneal surface (endothelium), in accordance with an embodiment of the present invention, respectively, before and after cell growth on the peripheral edge.
Figure 3B:
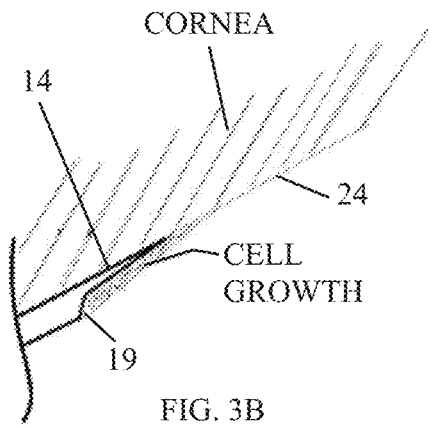

Reference is now made to FIGS. 3A and 3B, which illustrate the implant implanted on the posterior corneal surface 24, in accordance with an embodiment of the present invention, respectively, before and after cell growth on the peripheral edge. FIG. 3B shows that cells (e.g., epithelial cells) or proteins or other biomolecules created during the healing process, can proliferate radially inwards on peripheral edge 14 up to the stepped barrier 19 which blocks the cells or proteins or other biomolecules from growing on the central portion 12. The cells or proteins or other biomolecules help adhere the implant to the endothelium of the cornea.

The implant made of Ci26 has a swelling capacity of 26% water content. This process of material swelling is activated immediately after implant's hydration in saline. Once the implant is hydrated it becomes adhesive to proteins.

The edge 14 of the implant increases the adherence of corneal endothelial cells of the undamaged area of the corneal endothelium, which improves anchoring of the implant, which was demonstrated in histology assessment of post animal studies. The results demonstrate that adsorbed proteins (like fibronectin, collagen and more) mediate the attachment of the implant to the tissue. The Ci26 implant contains both hydrophilic and hydrophobic components in the implant material. The hydrophilic component is important for the wettability and the adjustment of the implant to the water environment right after implantation (otherwise the implant may be coated with air bubbles and may not permit interaction with the adsorbed proteins).

The average radius of the anterior corneal surface of a cornea with no reported edema has been measured as 7.79±0.27 (standard deviation) mm and the average radius of the posterior corneal surface has been measured as 6.53±0.25 mm. Both surfaces were found to be flatter horizontally than vertically. The asphericity of both the anterior and the posterior surface has been found to be independent of the radius of curvature, and there is no correlation between the asphericity of the anterior and the posterior corneal surface. As a result, the shape of the anterior corneal surface provides no definitive basis for knowing the asphericity of the posterior surface. Since the curvature and asphericity of the posterior corneal surface is not related to the outer (anterior) corneal surface, the change in radius of curvature of the posterior corneal surface is not obvious and not readily measurable. The present invention uniquely provides an implant that can accommodate any change in the radius of curvature of the posterior corneal surface.

The peripheral edge of the implant combines with the material properties of implant 10 to keep the implant 10 properly attached to the posterior surface of the cornea throughout the treatment. The peripheral edge, together with cell growth thereon, anchor the implant well to the posterior surface of the cornea at all stages of the thickness and radius of curvature of the cornea.

Figure 4A:
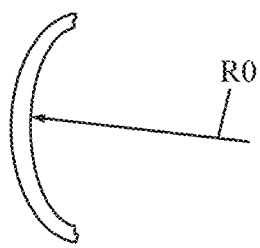
FIGS. 4A, 4B and 4C are simplified illustrations of the implant, respectively, before implantation in a patient (FIG. 4A), initially attached to the swollen and thickened posterior corneal surface (FIG. 4B), and attached after treating the edema (FIG. 4C).
Figure 4B:
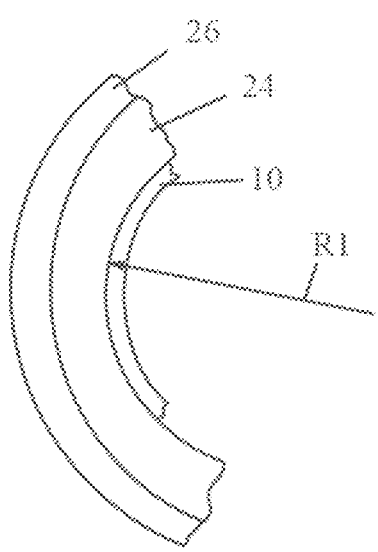
Figure 4C:
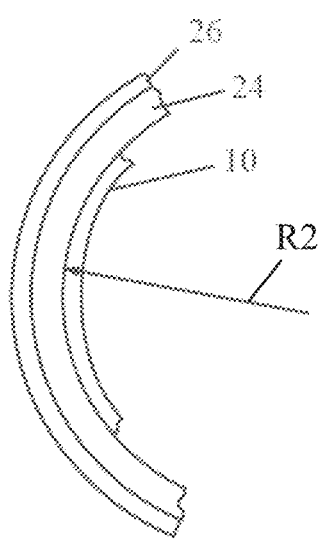

Reference is now made to FIGS. 4A, 4B and 4C, which illustrate that the implant may have three different basic radii of curvature. FIG. 4A illustrates the implant as provided by the manufacturer. At this stage, before use, the radius of curvature is denoted R0 and may be, without limitation, 6.0-8.0 mm.

FIG. 4B illustrates implant 10 initially attached to the posterior corneal surface 24, which is either the stroma and endothelium or just the stroma and FIG. 4C illustrates implant 10 attached to the posterior corneal surface after the corneal swelling has been reduced (which may be after several hours or one, two or more days, depending on the particular patient). Reference is also made to FIGS. 5A and 5B, which are simplified photographs of the implant, respectively, initially attached to the swollen and thickened posterior corneal surface, and attached after treating the edema.

It is seen in FIG. 4B, just after implantation that due to corneal edema, that the posterior corneal surface 24 and epithelium 26 are swollen and thickened. As seen in FIG. 5A, the edemal thickness in this example is 1139 µm. Due to the edemal swelling, the posterior corneal surface may become flattened as opposed to a normally thick cornea that is not swelled. This flattening effect causes the radius of curvature of the implant (R1 in FIG. 4B) to increase to at least 7 mm, and in some instances to between about 7-12 mm, and in many instances to between about 10-12 mm. The radius of curvature of the implant during healing is virtually the same as the radius of curvature of the posterior corneal surface.

FIG. 4C illustrates the effect of implant 10 attached to the posterior corneal surface 24 after treating the edema. FIG. 4C shows that the posterior corneal surface 24 and epithelium 26 have returned to normal thickness, without limitation, 556 µm (FIG. 5B). With the reduced thickness, as seen in FIG. 4C, the implant now has a radius of curvature R2, such as 6.53±0.25 mm (without limitation), which may be virtually the same as the radius of curvature of the posterior corneal surface 24.

Accordingly, the radius of curvature of implant 10 gradually changes from the initial implantation to a different radius of curvature after the corneal edema has been reduced. In most cases, due to the flattening of the cornea, R1 (edemal radius of curvature) is greater than R2 (post-edemal radius of curvature). However, the range of radial dimensions is not limited to this, and in some cases R2 may be greater than R1. In all cases, the material properties of implant 10 (such as, but not limited to, the material being annealed to remove internal stresses and toughen the material, the material being viscoelastic, the material's tensile strength, Young's modulus and elongation properties) enable the implant to change its radius of curvature to follow the contour of the healing cornea from the edemal state to the post-edemal state. Thus, the implant has the property of changing its radius of curvature from a first initially-implanted radius of curvature (R1) to a second post-treatment implanted radius of curvature (R2). The difference between the two radii of curvature R1 and R2 can be plus or minus 5-100%, without affecting the function of the implant.

It is noted that the as-manufactured (pre-implantation) radius of curvature of the implant (R0) can be the same as R2 or different therefrom, or can be the same as R1 or different therefrom.

Reference is now made to FIG. 6, which illustrates another possible feature of the implant of the invention. Instead of just one uniform radius of curvature, it is possible that the posterior corneal surface may be non-uniform with several different radii of curvature. Accordingly, the implant of the invention may accommodate itself to these multiple radii of curvature and have corresponding multiple radii of curvature, for example, without limitation, a central radius of curvature X1, and one or more radii of curvature Y1, Y2, and so forth, offset from the central radius of curvature X1. Each of these radii of curvature may have the above three values, that is, a first value as manufactured, a second value at initial implantation, and a third value post-treatment.

What is claimed is:

1. A device comprising:
an ocular implant constructed of a transparent, biologically compatible material and comprising a hydrophilic outer surface configured for continuous attachment to a posterior surface of a cornea, wherein said ocular implant has a first radius of curvature at initial attachment to the posterior surface of the cornea and a second radius of curvature at post-initial attachment to the posterior surface of the cornea, said first radius of curvature being different than said second radius of curvature, and wherein said ocular implant remains attached to the posterior surface of the cornea at both said first and second radii of curvature.

2. The device according to claim 1, wherein said ocular implant is constructed of a copolymer of hydroxyethyl methacrylate and methyl methacrylate.

3. The device according to claim 1, wherein said ocular implant is constructed of a random, crosslinked, acrylate based copolymer comprising poly[(methylmethacrylate)-co-(2-hydroxyethyl methacrylate)-co-(ethylene glycol dimethacrylate)].

4. The device according to claim 1, wherein said ocular implant is hydrated to have a water content of 26%±10%.

5. The device according to claim 1, wherein said ocular implant has a tensile strength of 2.5 MPa±10%.

6. The device according to claim 1, wherein said ocular implant has an elongation of 250%±10%.

7. The device according to claim 1, wherein said ocular implant has a refractive index of 1.458±10% @35° C.

8. The device according to claim 1, wherein said ocular implant comprises a central portion and a peripheral edge extending outwards from said central portion.

9. The device according to claim 8, wherein said peripheral edge is thinner than said central portion at a juncture of said peripheral edge with said central portion to form a stepped barrier at said juncture.

10. The device according to claim 8, wherein said peripheral edge is thinner at an outer radial edge thereof than at a juncture of said peripheral edge with said central portion.

11. The device according to claim 1, wherein said ocular implant is capable of everting.

12. A method for treating edema comprising:
providing said ocular implant of claim 1 and instructing to attach said ocular implant to the posterior surface of the cornea.

13. The method according to claim 12, wherein cells created during healing adhere to said ocular implant and cause said ocular implant to adhere to the cornea.

14. The method according to claim 12, wherein said ocular implant comprises a central portion and a peripheral edge extending outwards from said central portion, and cells created during healing adhere to said peripheral edge and adhere said ocular implant to the cornea.

15. The method according to claim 14, wherein said peripheral edge is thinner than said central portion at a juncture of said peripheral edge with said central portion to form a stepped barrier at said juncture, and said stepped barrier blocks cells from growing on said central portion.

16. The implant according to claim 1, wherein the first radius of curvature is larger than the second radius of curvature.

17. The implant according to claim 8, wherein a ratio between a length of said peripheral edge and a radius of said implant is 0.010-0.133:1.

18. The implant according to claim 1, wherein the first radius of curvature is smaller than the second radius of curvature.

19. The implant according to claim 1, wherein said implant is foldable for implantation through an incision of between about 1.8 mm and 3.0 mm.

20. The implant according to claim 1, wherein Young's modulus of said implant is 3.0 MPa±10%.

21. The implant according to claim 1, wherein said implant has a radius of curvature of between about 6.0 and 8.0 mm.

22. The implant according to claim 1, wherein said implant has multiple radii of curvature.

* * * * *